United States Patent
Elomari et al.

(10) Patent No.: US 7,723,556 B2
(45) Date of Patent: May 25, 2010

(54) PROCESS TO MAKE BASE OIL FROM THERMALLY CRACKED WAXY FEED USING IONIC LIQUID CATALYST

(75) Inventors: Saleh Elomari, Fairfield, CA (US); Russell R. Krug, Novato, CA (US); Stephen J. Miller, San Francisco, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 12/498,254

(22) Filed: Jul. 6, 2009

(65) Prior Publication Data

US 2009/0270667 A1 Oct. 29, 2009

Related U.S. Application Data

(63) Continuation-in-part of application No. 11/316,154, filed on Dec. 20, 2005, now Pat. No. 7,572,943, and a continuation-in-part of application No. 11/316,155, filed on Dec. 20, 2005, now Pat. No. 7,572,944, and a continuation-in-part of application No. 11/316,157, filed on Dec. 20, 2005, now Pat. No. 7,569,740, and a continuation-in-part of application No. 11/316,628, filed on Dec. 20, 2005, now Pat. No. 7,576,252, and a continuation-in-part of application No. 12/261,388, filed on Oct. 30, 2008.

(51) Int. Cl.
*C07C 2/68* (2006.01)
*C07C 2/70* (2006.01)
*C07C 2/60* (2006.01)

(52) U.S. Cl. .......... 585/722; 585/727; 585/728; 585/462; 585/463; 585/461

(58) Field of Classification Search ........... 585/722, 585/727, 728, 462, 463, 461
See application file for complete search history.

(56) References Cited

U.S. PATENT DOCUMENTS

| | | | |
|---|---|---|---|
| 5,750,455 | A | 5/1998 | Chauvin et al. |
| 6,028,024 | A | 2/2000 | Hirschauer et al. |
| 6,395,948 | B1 | 5/2002 | Hope et al. |
| 6,497,812 | B1 | 12/2002 | Schinski |
| 2007/0249883 | A1 | 10/2007 | Dakka et al. |
| 2009/0131731 | A1 | 5/2009 | Willams |

FOREIGN PATENT DOCUMENTS

EP 791643 8/2007

*Primary Examiner*—Thuan Dinh Dang
(74) *Attorney, Agent, or Firm*—Susan M. Abernathy; David M. Tuck

(57) ABSTRACT

We provide a process for making a base oil, comprising: a) selecting an olefin feed produced by thermal cracking of a waxy feed; b) oligomerizing the olefin feed in an ionic liquid oligomerization zone at a set of oligomerization conditions to form an oligomer; and c) alkylating the oligomer in the presence of an isoparaffin, in an ionic liquid alkylation zone, at a set of alkylation conditions to form an alkylated oligomeric product having a kinematic viscosity at 100° C. of 6.9 mm$^2$/s or greater, a VI of at least 134, and a Bromine Number of less than 4. We provide a process to make base oil from an olefin feed produced in a FCC unit. We also provide a process to make two or more viscosity grades of base oil from an olefin feed produced by thermal cracking of a waxy feed.

4 Claims, No Drawings

PROCESS TO MAKE BASE OIL FROM THERMALLY CRACKED WAXY FEED USING IONIC LIQUID CATALYST

This application is a continuation in part of U.S. patent application Ser. No. 11/316,154, filed Dec. 20, 2005, now U.S. Pat. No. 7,572,943; U.S. application Ser. No. 11/316,155, filed Dec. 20, 2005, now U.S. Pat. No. 7,572,944; U.S. application Ser. No. 11/316,157, filed Dec. 20, 2005, now U.S. Pat. No. 7,569,740; U.S. application Ser. No. 11/316,628, filed Dec. 20, 2005, now U.S. Pat. No. 7,576,252; and Ser. No. 12/261,388, filed Oct. 30, 2008: and herein incorporated in their entireties.

This application is related to a co-filed application, titled "PROCESS TO MAKE BASE OIL FROM FISCHER-TROPSCH CONDENSATE;" herein incorporated in its entirety.

SUMMARY OF THE INVENTION

We provide a process for making a base oil, comprising: a) selecting an olefin feed produced by thermal cracking of a waxy feed; b) oligomerizing the olefin feed in an ionic liquid oligomerization zone at a set of oligomerization conditions to form an oligomer; and c) alkylating the oligomer in the presence of an isoparaffin, in an ionic liquid alkylation zone, at a set of alkylation conditions to form an alkylated oligomeric product having a kinematic viscosity at 100° C. of 6.9 mm$^2$/s or greater, a VI of at least 134, and a Bromine Number of less than 4.

We provide a process for making a base oil, comprising: a) oligomerizing at least one olefin in an olefin feed produced in a FCC unit to produce an oligomerized product boiling in the middle distillate range; and b) alkylating the oligomerized product in an ionic liquid alkylation zone, at a set of alkylation conditions, to form an alkylated oligomeric product having a kinematic viscosity at 100° C. of 6.9 mm$^2$/s or greater and a VI of at least 134.

We also provide a process to make two or more viscosity grades of base oil, comprising: a) alkylating and oligomerizing an olefin feed produced by thermal cracking of a waxy feed with an acidic ionic liquid catalyst in an alkylation zone to produce an alkylated oligomeric product; and b) separating out two or more viscosity grades of base oil from the alkylated oligomeric product, wherein at least one of the two or more viscosity grades of base oil has:

i. a kinematic viscosity at 100° C. of 6.9 mm$^2$/s or greater,
ii. a VI of at least 134, and
iii. a Bromine Number of less than 4.

DETAILED DESCRIPTION OF THE INVENTION

In the present application the terms base oil, lubricant base oil, lubricant blendstock, and lubricant component are used to mean lubricant components that can be used to produce a finished lubricant.

The base oil is an alkylated oligomeric product. It can have a kinematic viscosity at 100° C. from about 1.5 mm$^2$/s to 30 mm$^2$/s. In some embodiments the base oil has a kinematic viscosity of 6.9 mm$^2$/s or greater. In other embodiments the process makes two or more viscosity grades of base oil. The two or more viscosity grades of base oil have kinematic viscosities at 100° C. from about 1.5 mm$^2$/s to 30 mm$^2$/s. Kinematic viscosity is measured by ASTM D 445.

A viscosity grade of base oil is base oil that differs from another viscosity grade of base oil by having a difference in kinematic viscosity at 100° C. of at least 0.5 mm$^2$/s. Examples of different viscosity grades of base oil are XXLN, XLN, LN, MN, and HN. An XXLN grade of base oil, when referred to in this disclosure, is a base oil having a kinematic viscosity at 100° C. between about 1.5 mm$^2$/s and about 2.3 mm$^2$/s. An XLN grade of base oil is a base oil having a kinematic viscosity at 100° C. between about 2.3 mm$^2$/s and about 3.5 mm$^2$/s. A LN grade of base oil is a base oil having a kinematic viscosity at 100° C. between about 3.5 mm$^2$/s and about 5.5 mm$^2$/s. A MN grade of base oil is a base oil having a kinematic viscosity at 100° C. between about 5.5 mm$^2$/s and about 10.0 mm$^2$/s. A HN grade of base oil is a base oil having a kinematic viscosity at 100° C. above 10 mm$^2$/s. Generally, the kinematic viscosity of a HN grade of base at 100° C. will be between about 10.0 mm$^2$/s and about 30.0 mm$^2$/s.

"Waxy feed" is a feed or stream comprising hydrocarbon molecules with a carbon number of C20+ and having a boiling point generally above about 600° F. (316° C.). A waxy feed contains at least 40 wt % normal paraffins, and in some embodiments may contain at least 50 wt % normal paraffins, or at least 75 wt % normal paraffins. The wt % normal paraffins are measured by a method described later in this specification. In some embodiments a major portion of the feed should boil above 650° F. In one embodiment at least 80 wt % of the feed will boil above 650° F., and in another embodiment at least 90 wt % will boil above 650° F. Waxy feeds typically will have an initial pour point above 0° C., or in other embodiments, above 10° C. Pour point is measured by ASTM D 5950-02 (Reapproved 2007).

The waxy feeds useful in the processes disclosed herein may be synthetic waxy feedstocks, such as Fischer Tropsch waxy hydrocarbons, or may be derived from natural sources. Accordingly, the waxy feeds to the processes may comprise Fischer Tropsch derived waxy feeds, petroleum waxes, waxy distillate stocks such as gas oils, lubricant oil stocks, high pour point polyalphaolefins, foots oils, normal alpha olefin waxes, slack waxes, deoiled waxes, microcrystalline waxes, and mixtures thereof.

Oligomerization of two or more olefin molecules results in the formation of an olefin oligomer that generally comprises a long branched chain molecule with one remaining double bond. In some embodiments the processes provide an improved way to reduce the concentration of double bonds and at the same time enhance the quality of the desired fuel or lubricant. The processes reduce the amount of hydrofinishing that may be needed to achieve a desired product with low olefin concentration. The olefin concentration can be determined by Bromine Index or Bromine Number. Bromine Number can be determined by test ASTM D 1159. Bromine Index can be determined by ASTM D 2710. Test methods D 1159 and ASTM D 2710 are incorporated herein by reference in their entirety. Bromine Index is effectively the number of milligrams of Bromine ($Br_2$) that react with 100 grams of sample under the conditions of the test. Bromine Number is effectively the number of grams of bromine that will react with 100 grams of specimen under the conditions of the test.

In one embodiment, HCl or a component that directly or indirectly supplies protons is added to either or both the oligomerization zone or the alkylation zone. Although not wishing to be limited by theory it is believed that the presence of a Brönsted acid such as HCl greatly enhances the acidity and, thus, the activity of the ionic liquid catalyst.

In one embodiment, the lubricant base oil or lubricant blendstock has reduced levels of olefins without hydrogenation or with minimal hydrofinishing. In some embodiments, the value of the resultant olefin oligomers is raised by increasing the molecular weight of the oligomer and increasing the branching by incorporation of isoparaffin groups into the oligomers' skeletons. These properties can both add significant value to the product, particularly when starting with a highly linear hydrocarbon. In some embodiments, the products can have a combination of highly desirable and novel qualities for a lubricant component or base oil, including having a very high VI with a very low cloud point while also having a fairly wide boiling range.

In some embodiments the alkylated oligomeric product has a low cloud point. The cloud point can be less than $-30°$ C., less than $-40°$ C., less than $-45°$ C., or less than $-50°$ C. In the past it has been very difficult to obtain low cloud points when making base oils from waxy feeds.

In one embodiment the alkylated oligomeric product has a broad boiling range. A broad boiling range is a difference between the T90 and T10 boiling points of at least $225°$ F. by SIMDIST. In some embodiments the alkylated oligomeric product has a difference between the T90 and T10 boiling points of at least $225°$ F., $250°$ F., $275°$ F., or $300°$ F. Because of the broad boiling range, the alkylated oligomeric product may comprise two or more viscosity grades of base oil. The different viscosity grades of base oil in the alkylated oligomeric product may be separated by vacuum distillation. One of the viscosity grades of base oil may be a distillate bottoms product.

Sometimes there is an increased demand for one viscosity grade of base oil. In some embodiments, the set of oligomerizing conditions or set of alkylating conditions are selected to optimize a yield of one of the two or more viscosity grades of base oil. For example the ratio of an isoparaffin to an olefin can be adjusted up to favor more alkylation and less oligomerization, such that a yield of a lighter viscosity grade of base oil is increased. Alternatively, the amount of a Brönsted acid in either the oligomerization zone or the alkylation zone may be adjusted to optimize a yield of one of the two or more viscosity grades of base oil.

In one embodiment the oligomerizing is dimerizing. In another embodiment the oligomerizing brings together more than two olefins, so it is more than dimerizing.

In one embodiment, the oligomerized product boils in the middle distillate range. A "middle distillate" is a hydrocarbon product having a boiling range between $250°$ F. and $700°$ F. ($121°$ C. and $371°$ C.). The term "middle distillate" includes the diesel, heating oil, jet fuel, and kerosene boiling range fractions. It may also include a portion of naphtha or light oil. A "naphtha" is a lighter hydrocarbon product having a boiling range between $100°$ F. and $400°$ F. ($38°$ C. and $204°$ C.).

In one embodiment the oligomerized product has lower amounts of heteroatoms than in the olefin feed. Examples of heteroatoms are nitrogen, sulfur, and oxygen. Lower amounts of heteroatoms are desired in base oil. It is also desirable to have lower amounts of heteroatoms in some embodiments, as they can interfere with the alkylating step of the process.

In one embodiment the process uses an ionic liquid catalyst to alkylate an oligomerized olefin with an isoparaffin under relatively mild conditions. For example, in one embodiment the heat of reaction during the alkylating remains at $100°$ C. or less, at $75°$ C. or less, at $50°$ C. or less, or at $25°$ C. or less. The alkylation optionally can occur under effectively the same conditions as oligomerization. This finding that alkylation and oligomerization reactions can occur using effectively the same ionic liquid catalyst system and optionally under similar or even the same conditions can be used to make a highly integrated, synergistic process resulting in an alkylated oligomer product having desirable properties. Also in a particular embodiment the alkylation and oligomerization reactions can occur simultaneously under the same conditions.

In some embodiments the ionic liquid oligomerization zone, or the ionic liquid alkylation zone, comprises an acidic chloroaluminate ionic liquid catalyst. In some embodiments both the ionic liquid oligomerization and the ionic liquid alkylation zones comprise an acidic chloroaluminate ionic liquid catalyst. In some embodiments, the same acidic chloroaluminate ionic liquid catalyst is used in both zones.

In some embodiments the acidic chloroaluminate ionic liquid catalyst is used in the presence of a Brönsted acid. The Brönsted acid may be a halohalide such as hydrogen chloride. Other promoters such as alkyl halides or metal halides may be added to the oligomerization or alkylation zones.

The oligomerization reaction and the alkylation reaction can be performed concurrently or separately. An advantage of combining the oligomerization and alkylation is lower capital and operating costs. An advantage of the 2 step process (oligomerization followed by alkylation in a separate zone) is that the two separate reaction zones can be optimized independently. Thus the conditions for oligomerization zones can be different than the alkylation zone conditions. Also the ionic liquid catalyst can be different in the different zones. For instance, it may be preferable to make the alkylation zone more acidic than the oligomerization zone. This may involve the use of an entirely different ionic liquid catalyst in the two zones or one of the zones can be modified, for example, by the addition of a Brönsted acid to the alkylation zone.

In one embodiment, the ionic liquid catalysts used in the alkylation zone and in the oligomerization zone are the same. This helps save on catalyst costs, potential contamination issues, and provides synergy opportunities in the process.

In some embodiments, the process produces a product having a very low cloud point and a very high VI. Cloud Point can be determined by ASTM D 2500. VI can be determined by ASTM D 2270. ASTM test methods D 2500 and D D2270 are incorporated by reference herein in their entirety.

In the present application, distillation data was generated for several of the products by SIMDIST. SIMDIST involves the use of ASTM D 6352 or ASTM D 2887 as appropriate. ASTM D 6352 and ASTM D 2887 are incorporated herein by reference in their entirety. Distillation data can also be generated using ASTM D86 which is incorporated herein by reference in its entirety.

Ionic Liquids

Ionic liquids are a class of compounds made up entirely of ions and are generally liquids at ambient and near ambient temperatures. Often salts which are composed entirely of ions are solids with high melting points, for example, above $450°$ C. These solids are commonly known as 'molten salts' when heated to above their melting points. Sodium chloride, for example, is a common 'molten salt', with a melting point of $800°$ C. Ionic liquids differ from 'molten salts', in that they have low melting points, for example, from $-100°$ C. to $200°$ C. Ionic liquids tend to be liquids over a very wide temperature range, with some having a liquid range of up to $300°$ C. or higher. Ionic liquids are generally non-volatile, with effectively no vapor pressure. Many are air and water stable, and can be good solvents for a wide variety of inorganic, organic, and polymeric materials.

The properties of ionic liquids can be tailored by varying the cation and anion pairing. Ionic liquids and some of their commercial applications are described, for example, in J. Chem. Tech. Biotechnol, 68:351-356 (1997); J. Phys. Condensed Matter, 5:(supp 34B):B99-B106 (1993); Chemical and Engineering News, Mar. 30, 1998, 32-37; J. Mater.

Chem., *:2627-2636 (1998); and Chem. Rev., 99:2071-2084 (1999), the contents of which are hereby incorporated by reference.

Many ionic liquids are amine-based. Among the most common ionic liquids are those formed by reacting a nitrogen-containing heterocyclic ring (cyclic amines), preferably nitrogen-containing aromatic rings (aromatic amines), with an alkylating agent (for example, an alkyl halide) to form a quaternary ammonium salt, followed by ion exchange with Lewis acids or halide salts, or by anionic metathesis reactions with the appropriate anion sources to introduce the desired counter anionic to form ionic liquids. Examples of suitable heteroaromatic rings include pyridine and its derivatives, imidazole and its derivatives, and pyrrole and its derivatives. These rings can be alkylated with varying alkylating agents to incorporate a broad range of alkyl groups on the nitrogen including straight, branched or cyclic $C_{1-20}$ alkyl group, but preferably $C_{1-12}$ alkyl groups since alkyl groups larger than $C_1$-$C_{12}$ may produce undesirable solid products rather than ionic liquids. Pyridinium and imidazolium-based ionic liquids are perhaps the most commonly used ionic liquids. Other amine-based ionic liquids including cyclic and non-cyclic quaternary ammonium salts are frequently used. Phosphonium and sulphonium-based ionic liquids have also been used.

Counter anions which have been used include chloroaluminate, bromoaluminate, gallium chloride, tetrafluoroborate, tetrachloroborate, hexafluorophosphate, nitrate, trifluoromethane sulfonate, methylsulfonate, p-toluenesulfonate, hexafluoroantimonate, hexafluoroarsenate, tetrachloroaluminate, tetrabromoaluminate, perchlorate, hydroxide anion, copper dichloride anion, iron trichloride anion, antimony hexafluoride, copper dichloride anion, zinc trichloride anion, as well as various lanthanum, potassium, lithium, nickel, cobalt, manganese, and other metal ions. In some embodiments, the ionic liquid catalysts are acidic haloaluminates, such as acidic chloroaluminate ionic liquid catalysts.

In some embodiments, the organic cations in the ionic liquid catalysts can be selected from the group consisting of pyridinium-based and imidazolium-based cations.

In one embodiment, the acidic chloroaluminate ionic liquid catalyst is an acidic pyridinium chloroaluminate. Examples are alkyl-pyridinium chloroaluminates. In one embodiment, the acidic chloroaluminate ionic liquid catalyst is an alkyl-pyridinium chloroaluminate having a single linear alkyl group of 2 to 6 carbon atoms in length. One particular acidic chloroaluminate ionic liquid catalyst that has proven effective is 1-butyl-pyridinium chloroaluminate.

In one embodiment, 1-butyl-pyridinium chloroaluminate is used in the presence of a Brönsted acid. Not to be limited by theory, the Brönsted acid acts as a promoter or co-catalyst. Examples of Brönsted acids are Sulfuric acid, HCl, HBr, HF, Phosphoric acid, HI, etc. Other protic acids or species that directly or indirectly aid in supplying protons may also be used as Brönsted acids or in place of Brönsted acids.

The Feeds

In the process of the present invention one of the important feedstocks comprises an olefin feed produced by thermal cracking of a waxy feed. The olefinic group provides the reactive sites for the oligomerization reaction as well as for the alkylation reaction. The olefin feed can be a fairly pure olefinic hydrocarbon cut or can be a mixture of hydrocarbons having different chain lengths, and thus a wide boiling range. The olefinic hydrocarbons in the olefin feed can be terminal olefins (alpha olefin) or can be internal olefins (internal double bond). The olefinic hydrocarbons in the olefin feed can be either straight chain, branched, or a mixture of both. The olefin feed can include unreactive diluents such as normal paraffins.

In one embodiment of the present invention, the olefin feed comprises olefins in a range of C2 to C30, such as C2 to C7, C5 to C8, or C5 to C15. An example of an olefin feed with olefins in a range of C5 to C15 is FCC naphtha. Another example is FCC gasoline. An example of an olefin feed with olefins in a range of C2 to C5 or C2 to C7 is FCC gas. In some embodiments, certain ranges of olefins may be separated from the effluent from a thermal hydrocracking process to optimize the process economics and to select a range of olefins that will produce a desired alkylated oligomeric product. In some embodiments the olefin feed produced by thermal cracking of a waxy feed will also comprise isoparaffins. In some embodiments, the isoparaffins may be separated out from the olefin feed. In other embodiments, they may not be separated out from the olefin feed.

In one embodiment, the olefin feed is produced by thermal cracking of a waxy feed to make one or more thermally cracked hydrocarbons. Thermally cracked hydrocarbons may be cracked wax, such as cracked wax from a Fischer-Tropsch (FT) process or thermally cracked petroleum wax. A process for making olefins by cracking FT products is disclosed in U.S. Pat. No. 6,497,812 which is incorporated herein by reference in its entirety. In one embodiment the olefin feed is produced by autothermally cracking a waxy hydrocarbon feedstream which has been selected to produce high yields of linear alpha-olefins while enabling relatively easy separation of desired linear alpha-olefins in high purity. A process for autothermally cracking a waxy hydrocarbon feedstream to produce olefin feeds is disclosed in US Patent Application No. 20090131731A1, herein incorporated in its entirety by reference.

In one embodiment, the olefin feed may be from a FCC unit or a coker. In other embodiments, the olefin feed may be from a wax cracker, such as an autothermal cracking reactor. Olefins are typically produced in petroleum refineries using either the FCC process, the delayed coking process, or less often the fluidized coking process. In the future, as more waxy feeds become available from new sources (such as from Fischer-Tropsch processes such as Gas-to-Liquid, Coal-to-Liquid, or Biomass-to-Liquid), wax crackers will become more economic. FCC units use a fluidized catalyst system to facilitate catalyst and heat transfer between a reactor and a regenerator. Combustion of coke in the regenerator provides the heat necessary for the reactor. A good overview of examples of FCC units are described in "UOP Fluid Catalytic Cracking (FCC) and Related Processes", UOP 4523-7, June 2008; herein incorporated in its entirety.

A delayed or fluidized coker is an oil refinery processing unit that converts the residual oil from a vacuum distillation column or an atmospheric distillation column into low molecular weight hydrocarbon gases, naphtha, light and heavy gas oils, and petroleum coke. The process thermally cracks the long chain hydrocarbon molecules in the residual oil feed into shorter chain molecules. The coke from a coker can either be fuel grade (high in sulphur and metals) or anode grade (low in sulphur and metals).

The shorter chain molecules produced in a coker are richer in alpha olefin content than olefin feeds from a FCC unit. The high alpha olefin content in the shorter chain molecules produced in a coker unit form because cokers crack primarily by electron-promoted free radical mechanisms, whereas a FCC unit cracks by proton-promoted acid mechanisms. The shorter chain molecules from a coker also have a relatively high concentration of olefins. The higher the normal-paraffin content in the feed to the coker unit, the greater the alpha olefin content of the shorter chain molecules produced in the coker unit. In one embodiment, an olefin feed from a coker unit are valuable feeds to make base oil as they are not generally used to make alkylate gasoline blend stock due to their high concentration of alpha olefins.

In one embodiment the coker unit is a delayed coker unit. A delayed coker unit is a type of coker unit whose process consists of heating a residual oil feed to its thermal cracking temperature in a furnace with multiple parallel passes. This cracks the heavy, long chain hydrocarbon molecules of the residual oil into coker gas oil and petroleum coke.

Delayed coker units may provide a higher content of alpha olefins than feeds from a FCC unit. The content of the alpha olefins is dependent on the normal-paraffin content in the feed to the delayed coker unit. Many oil refineries have delayed coker units and the shorter chain molecules produced in the delayed coker units are not in as high demand for conventional sulfuric or HF alkylation plants or for chemicals, so their availability and pricing are favorable. In some embodiments, the shorter chain molecules produced in a delayed coker unit will require a clean-up step to reduce nitrogen and sulfur-containing hydrocarbons before the oligomerizing step of the process.

Another important feedstock is an isoparaffin. The simplest isoparaffin is isobutane. Isopentanes, isohexanes, isoheptanes, and other higher isoparaffins are also useable in the process of the present invention. Economics and availability are the main drivers of the isoparaffins selection. Lighter isoparaffins tend to be less expensive and more available due to their low gasoline blend value (due to their relatively high vapor pressure). Mixtures of light isoparaffins can also be used in the present invention. Mixtures such as $C_4$-$C_5$ isoparaffins can be used and may be advantaged because of reduced separation costs. The isoparaffins feed stream may also contain diluents such as normal paraffins. This can be a cost savings, by reducing the cost of separating isoparaffins from close boiling paraffins. Normal paraffins will tend to be unreactive diluents in the process of the present invention.

In an optional embodiment the resultant alkylated oligomer can be hydrogenated to further decrease the concentration of olefins and thus the Bromine Number. After hydrogenation, the lubricant component or base oil has a Bromine Number of less than 0.8, for example less than 0.5, less than 0.3, or less than 0.2.

In one embodiment the alkylation conditions include a temperature of from about 15 to about 200° C., such as from about 20 to about 150° C., from about 25 to about 100, or from 50 to 100° C.

In one embodiment, the oligomerization conditions include a temperature of from about 0 to about 150° C., such as from about 10 to about 100° C., or from about 0 to about 50° C.

As discussed elsewhere the oligomerization and the alkylation can occur separately (in separate optimized zones) or concurrently. In the embodiment where the alkylation and oligomerization occur concurrently, optimum conditions for either reaction may have to be compromised. However, surprisingly the conditions can be adjusted to achieve both substantial oligomerization and alkylation and result in a valuable lubricant base oil or blendstock.

Wt % Normal Paraffins in Waxy Feeds

Quantitative analysis of normal paraffins in waxy feeds is determined by gas chromatography (GC). The GC (Agilent 6890 or 5890 with capillary split/splitless inlet and flame ionization detector) is equipped with a flame ionization detector, which is highly sensitive to hydrocarbons. The method utilizes a methyl silicone capillary column, routinely used to separate hydrocarbon mixtures by boiling point. The column is fused silica, 100% methyl silicone, 30 meters length, 0.25 mm ID, 0.1 micron film thickness supplied by Agilent. Helium is the carrier gas (2 ml/min) and hydrogen and air are used as the fuel to the flame.

The waxy feed is melted to obtain a 0.1 g homogeneous sample. The sample is immediately dissolved in carbon disulfide to give a 2 wt % solution. If necessary, the solution is heated until visually clear and free of solids, and then injected into the GC. The methyl silicone column is heated using the following temperature program: Initial temp: 150° C. (If C7 to C15 hydrocarbons are present, the initial temperature is 50° C.) Ramp: 6° C. per minute Final Temp: 400° C. Final hold: 5 minutes or until peaks no longer elute The column then effectively separates, in the order of rising carbon number, the normal paraffins from the non-normal paraffins. A known reference standard is analyzed in the same manner to establish elution times of the specific normal-paraffin peaks. The standard is ASTM D2887 n-paraffin standard, purchased from a vendor (Agilent or Supelco), spiked with 5 wt % Polywax 500 polyethylene (purchased from Petrolite Corporation in Oklahoma). The standard is melted prior to injection. Historical data collected from the analysis of the reference standard also guarantees the resolving efficiency of the capillary column.

If present in the sample, normal paraffin peaks are well separated and easily identifiable from other hydrocarbon types present in the sample. Those peaks eluting outside the retention time of the normal paraffins are called non-normal paraffins. The total sample is integrated using baseline hold from start to end of run. N-paraffins are skimmed from the total area and are integrated from valley to valley. All peaks detected are normalized to 100%. EZChrom is used for the peak identification and calculation of results.

In summary, some of the potential benefits of the processes include,

Reduced capital cost for hydrotreating or hydrofinishing,
Lower operating costs due to reduced hydrogen and extensive hydrogenation requirements,
Potential use of the same ionic liquid catalyst for oligomerization and alkylation steps,
Improved branching characteristics of the product,
Increased overall molecular weight of the product,
Incorporation of low cost feed (isoparaffins) to increase liquid yield of high value distillate fuel or lubricant components,
Production of a base oil or lubricant component having unique, high value properties,
Upgrading of olefin feeds from a FCC unit or a coker,
The ability to make two or more viscosity grades of base oil with improved properties.

For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All of the publications, patents and patent applications cited in this application are herein incorporated by reference in their entirety to the same extent as if the disclosure of each individual publication, patent application or patent was specifically and individually indicated to be incorporated by reference in its entirety.

This written description uses examples to disclose the invention, including the best mode, and also to enable any person skilled in the art to make and use the invention. Many modifications of the exemplary embodiments of the invention disclosed above will readily occur to those skilled in the art. Accordingly, the invention is to be construed as including all structure and methods that fall within the scope of the appended claims.

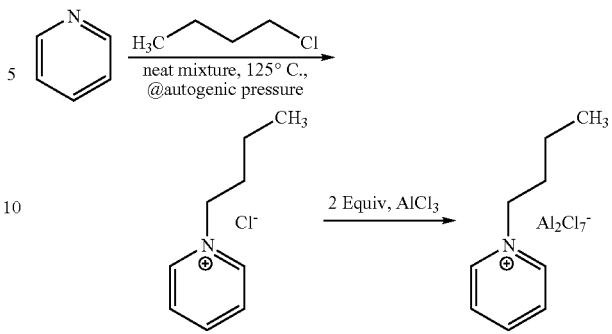

EXAMPLES

Example 1

Preparation of Fresh 1-Butyl-pyridinium Chloroaluminate Ionic Liquid 1-butyl-pyridinium chloroaluminate is a room temperature ionic liquid prepared by mixing neat 1-butyl-pyridinium chloride (a solid) with neat solid aluminum trichloride in an inert atmosphere. The syntheses of 1-butyl-pyridinium chloride and the corresponding 1-butyl-pyridinium chloroaluminate are described below. In a 2-L Teflon-lined autoclave, 400 gm (5.05 mol.) anhydrous pyridine (99.9% pure purchased from Aldrich) were mixed with 650 gm (7 mol.) 1-chlorobutane (99.5% pure purchased from Aldrich). The neat mixture was sealed and let to stir at 125° C. under autogenic pressure over night. After cooling off the autoclave and venting it, the reaction mix was diluted and dissolved in chloroform and transferred to a three liter round bottom flask. Concentration of the reaction mixture at reduced pressure on a rotary evaporator (in a hot water bath) to remove excess chloride, un-reacted pyridine and the chloroform solvent gave a tan solid product. Purification of the product was done by dissolving the obtained solids in hot acetone and precipitating the pure product through cooling and addition of diethyl ether. Filtering and drying under vacuum and heat on a rotary evaporator gave 750 gm (88% yields) of the desired product as an off-white shinny solid. $^{1}$H-NMR and $^{13}$C-NMR were ideal for the desired 1-butyl-pyridinium chloride and no presence of impurities was observed by NMR analysis.

1-Butyl-pyridinium chloroaluminate was prepared by slowly mixing dried 1-butyl-pyridinium chloride and anhydrous aluminum chloride ($AlCl_3$) according to the following procedure. The 1-butyl-pyridinium chloride (prepared as described above) was dried under vacuum at 80° C. for 48 hours to get rid of residual water (1-butyl-pyridinium chloride is hydroscopic and readily absorbs water from exposure to air). Five hundred grams (2.91 mol.) of the dried 1-butyl-pyridinium chloride were transferred to a 2-Liter beaker in a nitrogen atmosphere in a glove box. Then, 777.4 gm (5.83 mol.) of anhydrous powdered $AlCl_3$ (99.99% from Aldrich) were added in small portions (while stirring) to control the temperature of the highly exothermic reaction. Once all the $AlCl_3$ was added, the resulting amber-looking liquid was left to gently stir overnight in the glove box. The liquid was then filtered to remove any un-dissolved $AlCl_3$. The resulting acidic 1-butyl-pyridinium chloroaluminate was used as the catalyst for the Examples in the Present Application.

Example 2

Oligomerization of 1-Decene

One process for making high quality oils is by oligomerization of olefins followed by a separate step of alkylation with an isoparaffin. Olefin oligomers exhibit good physical lubricating properties. However, introducing short chain branching in the oligomers enhances the properties of the final products. Introducing the branching can be done by alkylation of the oligomers with isoparaffins. Alkylation of the oligomeric products is also a route to reducing the olefinicity of the oligomers and, hence, producing chemically and thermally more stable oligomers. The process is exemplified by alkylation of 1-decene oligomers (described below).

Oligomerization of 1-decene and alkylation of the oligomer were done according to the procedures described below. In a 300 cc autoclave equipped with an overhead stirrer, 100 gm of 1-decene was mixed in with 20 gm of 1-methyl-tributyl ammonium chloroaluminate. A small amount of HCl (0.35 gm) was introduced to the mix as a promoter and the reaction mix was heated to 50° C. with vigorous stirring for 1 hr. Then, the stirring was stopped and the reaction was cooled down to room temperature and let to settle. The organic layer (insoluble in the ionic liquid) was decanted off and washed with 0.1N KOH. The organic layer was separated and dried over anhydrous $MgSO_4$. The colorless oily substance was analyzed by SIMDIST. The oligomeric product has a Bromine Number of 7.9. Table 1 below shows the SIMDIST analysis of the oligomerization products.

Example 3

Alkylations of 1-Decene Oligomers

The oligomers of 1-decene made as described in example 2 were alkylated with isobutane in 1-butylpyridinium chloroaluminate and in methyl-tributyl ammonium chloroaluminate (TBMA) ionic liquids according to the procedures described below. In a 300 cc autoclave fitted with an overhead stirrer, 26 gm of the oligomer and 102 gm of isobutane were added to 21 gm of methyl-tributyl-ammonium chloroaluminate ionic liquid. To this mixture, 0.3 gm of HCl gas was added and the reaction was heated to 50° C. for 1 hr while stirring at >1000 rpm. Then the reaction was stopped and the products were collected in a similar procedure as described above for the oligomerization reaction. The collected products, colorless oils, have a Bromine Number of 3.2. Table 1 shows the SIM-DIST analysis of the oligomer alkylation products.

Alkylation of the oligomer was repeated using the same procedure described above, but 1-butylpyridinium chloroaluminate was used in place of methyl-tributyl-ammonium chloroaluminate. Alkylation of the oligomer in butylpyridinium gave a product with a bromine index of 2.7. The SIMDIST data is shown in Table 1.

TABLE 1

| SIMDIST TBP (WT %) | 1-Decene Oligomers ° F. | 1-Decene oligomers Alkylation in 1-butylpyridinium chloroaluminate | 1-Decene oligomers alkylation in TBMA |
|---|---|---|---|
| TBP@0.5 | 330 | 298 | 296 |
| TBP@5 | 608 | 341 | 350 |
| TBP@10 | 764 | 574 | 541 |
| TBP@15 | 789 | 644 | 630 |
| TBP@20 | 856 | 780 | 756 |
| TBP@30 | 944 | 876 | 854 |
| TBP@40 | 1018 | 970 | 960 |
| TBP@50 | 1053 | 1051 | 1050 |
| TBP@60 | 1140 | 1114 | 1118 |
| TBP@70 | 1192 | 1167 | 1173 |
| TBP@80 | 1250 | 1213 | 1220 |
| TBP@90 | 1311 | 1263 | 1268 |
| TBP@95 | 1340 | 1287 | 1291 |
| TBP@99.5 | 1371 | 1312 | 1315 |

Example 4

Oligomerization of 1-Decene in Ionic Liquids in the Presence of iso-Butane

Oligomerization of 1-decene was carried out in acidic 1-butyl-pyridinium chloroaluminate in the presence of 10 mole % of isobutane. The reaction was done in the presence of HCl as a promoter. The procedure below describes, in general, the process. To 42 gm of 1-butyl-pyridinium chloroaluminate in a 300 cc autoclave fitted to an overhead stirrer, 101 gm of 1-decene and 4.6 gm of isobutane were added and the autoclave was sealed. Then 0.4 gm of HCl was introduced and the stirring started. The reaction was heated to 50° C. The reaction was exothermic and the temperature quickly jumped to 88° C. The temperature in few minutes went back down to 44° C. and was brought up to 50° C. and the reaction was vigorously stirred at about 1200 rpm for an hour at the autogenic pressure (~atmospheric pressure in this case). Then, the stirring was stopped and the reaction was cooled to room temperature. The contents were allowed to settle and the organic layer (immiscible in the ionic liquid) was decanted off and washed with 0.1N KOH aqueous solution. The colorless oil was analyzed with simulated distillation and bromine analysis. The Bromine Number was 2.6. The Bromine Number is much less than that usually observed for the 1-decene oligomerization in the absence of isobutane. The Bromine Number for 1-decene oligomerization in the absence of $iC_4$ is in the range of 7.5-7.9 based on the catalyst, contact time and catalyst amounts used in the oligomerization reaction. The Simulated Distillation data is shown in Table 3.

The Simulated Distillation data in Tables 1 and 3 show that alkylations of the already made 1-decene oligomers with isobutane and the simultaneous oligomerization/alkylation of 1-decene lead to fairly comparable products. The overall outcome of the two operations is amazingly close in the products boiling ranges and olefinic contents as indicated by bromine numbers shown in Table 2.

Table 2 compares the Bromine Numbers of the starting 1-decene, 1-decene oligomerization products in the presence of $iC_4$, 1-decene oligomerization products without $iC_4$, and the alkylation products of 1-decene oligomers with excess $iC_4$.

TABLE 2

| Material | 1-Decene | Oligomerization-alkylation of 1-Decene with 10 mol % $iC_4$ | Oligomerization Products of 1-Decene/No $iC_4$ | Alkylated 1-decene oligomers |
|---|---|---|---|---|
| Bromine Number | 114 | 2.6 | 7.9 | 2.8 |

The data above suggests that the chemistry can be done by either alkylating the oligomers in situ (where isoparaffins are introduced into the oligomerization reactor) or in consecutive steps to oligomerization of an alpha olefin. In both processes, the yielded products are close in their properties. In the simultaneous oligomerization-alkylation scheme, the desired alkylated oligomeric products can be made in one single step and, thus, can be an economically advantageous process. However, the two step process with two separate reaction zones where each can be optimized independently, provides greater chances for tailoring and tuning the conditions to make products with particularly desired properties.

Example 5

Oligomerization of 1-Decene in Ionic Liquids in the Presence of Varying iso-Butane Concentrations Oligomerization of 1-decene was carried out in acidic 1-butyl-pyridinium chloroaluminate in the presence of varying mole % of isobutane. The reaction was done in the presence of HCl as a promoter (co-catalyst). The procedure below describes, in general, the process. To 42 gm of 1-butyl-pyridinium chloroaluminate in a 300 cc autoclave fitted to an overhead stirrer, 101 gm of 1-decene and 4.6 gm of isobutane were added and the autoclave was sealed. Then 0.2-0.5 gm of HCl was introduced into the reactor, and then, started the stirring. The reaction is exothermic and the temperature quickly jumped to 88° C. The temperature dropped down quickly to the mid 40s and was brought up to 50° C. and kept at around 50° C. for the remainder of the reaction time. The reaction was vigorously stirred for about an hour at the autogenic pressure. The stirring was stopped, and the reaction was cooled to room temperature. The contents were allowed to settle and the organic layer (immiscible in the ionic liquid) was decanted off and washed with 0.1N KOH aqueous solution. The recovered oils were characterized with simulated distillation, bromine analysis, viscosity, viscosity indices, and pour and cloud points.

Table 3, below, show the properties of the resulting oils of different 1-decene/isobutane ratios. All the reactions were run for approximately 1 hr at 50° C. in the presence of 20 gm of ionic liquid catalyst.

TABLE 3

| n | $C_{10}^=/iC4 = 0.8$ | $C_{10}^=/iC_4 = 1$ | $C_{10}^=/iC_4 = 4$ | $C_{10}^=/iC_4 = 5.5$ | $C_{10}^=/iC_4 = 9$ |
|---|---|---|---|---|---|
| TBP @0.5 | 301 | 311 | 322 | 329 | 331 |
| TBP @5 | 340 | 382 | 539 | 605 | 611 |
| TBP @10 | 440 | 453 | 663 | 746 | 775 |
| TBP @20 | 612 | 683 | 792 | 836 | 896 |
| TBP @30 | 798 | 842 | 894 | 928 | 986 |
| TBP @40 | 931 | 970 | 963 | 999 | 1054 |
| TBP @50 | 1031 | 1041 | 1007 | 1059 | 1105 |
| TBP @60 | 1098 | 1099 | 1067 | 1107 | 1148 |
| TBP @70 | 1155 | 1154 | 1120 | 1154 | 1187 |
| TBP @80 | 1206 | 1205 | 1176 | 1200 | 1228 |

TABLE 3-continued

| n | $C_{10}^=/iC4 = 0.8$ | $C_{10}^=/iC_4 = 1$ | $C_{10}^=/iC_4 = 4$ | $C_{10}^=/iC_4 = 5.5$ | $C_{10}^=/iC_4 = 9$ |
|---|---|---|---|---|---|
| TBP @90 | 1258 | 1260 | 1242 | 1252 | 1278 |
| TBP @95 | 1284 | 1290 | 1281 | 1282 | 1305 |
| TBP @99.5 | 1311 | 1326 | 1324 | 1313 | 1335 |

The data shown in Table 3 indicates that the amount of isobutane added to the reaction does influence the boiling range of the produced oils. As shown in Table 3, there are more products in the lower boiling cuts when higher concentrations of isobutane are used in the reaction. This indicates that more alkylation is taking part directly with 1-decene and 1-decene dimers rather than with higher oligomers when higher isobutane concentrations are present in the reaction zone. When more isobutane is present more alkylation can occur, and 1-decene alkylation with $iC_4$ to make $C_{14}$ and 1-decene dimer alkylation to make $C_{24}$ will be more prevalent than at lower concentrations of isobutane. Therefore, the degree of branching and oligomerization can be tailored by the choice of olefins, isoparaffins, olefin/isoparaffin ratios, contact time and the reaction conditions.

The alkylated oligomers will no longer take part in further oligomerization due to "capping" off their olefinic sites, and the final oligomeric chain will be shorter perhaps than the normal oligomeric products, but with more branching. While the oligomerization pathway is the dominant mechanism, it is very clear that the alkylation of 1-decene and its oligomers with isobutane does take part in the chemistry.

Table 4, below, compares some physical properties of the products obtained from the reactions of Table 3.

TABLE 4

| | $C10^=/iC_4 = 0.8$ | $C10^=/iC_4 = 1$ | $C10^=/iC_4 = 4$ | $C10^=/iC_4 = 5.5$ | $C10^=/iC_4 = 9$ |
|---|---|---|---|---|---|
| VI | 145 | 171 | 148 | 190 | 150 |
| Vis@100 | 9.84 | 7.507 | 9.73 | 7.27 | 11.14 |
| VIS@40 | 61.27 | 37.7 | 59.63 | 33.5 | 70.21 |
| Pour Point | −42 | −42 | −44 | −44 | −52 |
| Cloud Point | −63 | −64 | −66 | −69 | −28 |
| Bromine Number | 3.1 | 0.79 | 2.2 | 3.8 | 6.1 |

The oligomerization/alkylation run @ 1-decene/$iC_4$ ratio of 5.5 was repeated several times at the same feed ratios and conditions. The viscosity@100° C. in the repeated samples ranged from 6.9-11.2 cSt. The VI ranged from 156-172. All the repeated samples contained low boiling cuts (below 775° F.) ranging from 10%-15%. The low boiling cut appears to influence the VI.

The Bromine Numbers shown in Table 4 are much less than usually observed for the 1-decene oligomerization in the absence of isobutane. The Bromine Number for 1-decene oligomerization in the absence of $iC_4$ is in the range of 7.5-7.9 based on the catalyst, contact time and catalyst amounts used in the oligomerization reaction. Table 5, below, compares the Bromine Number analysis of 1-decene, simultaneous oligomerization and alkylation of 1-decene, 1-decene oligomerization only products, and the alkylated oligomers (oligomerization followed by alkylation). By looking at these values, one can see the role of the incorporation of isobutane on the olefinicity of the final products.

TABLE 5

| Material | 1-Decene | Oligomerization with 10 mol % $iC_4$, (20 mol % $iC_4$) | 1-Decene Oligomerization | Alkylated 1-decene oligomers with $iC_4$ |
|---|---|---|---|---|
| Bromine Number | 114 | 6.1, (2.2) | 7.9 | 2.8 |

Example 6

Oligomerization of a Mixture of Alpha Olefins in the Presence of iso-Butane

A 1:1:1 mixture of 1-hexene:1-octene:1-decene was oligomerised in the presence of isobutane at the reaction conditions described earlier for oligomerization of 1-decene in the presence of isobutane (100 gm olefins, 20 gm IL catalyst, 0.25 gm HCl as co-catalyst, 50° C., autogenic pressure, 1 hr). The products were separated from the IL catalyst, and the IL layer was rinsed with hexane, which was decanted off and added to the products. The products and the hexane wash were treated with 0.1N NaOH to remove any residual $AlCl_3$. The organic layers were collected and dried over anhydrous $MgSO_4$. Concentration (on a rotary evaporator at reduced pressure, in a water bath at ~70° C.) gave the oligomeric product as viscous yellow oils. Table 6 below shows the Simulated Distillation, viscosity, and pour point, cloud point, and bromine number data of the alkylated oligomeric products of the olefinic mixture in the presence of isobutane.

TABLE 6

| SIMDIST TBP (WT %), | Oligomers of $C_6^=, C_8^=, C_{10}^=$ W/$iC_4$ ° F. |
|---|---|
| TBP @0.5 | 313 |
| TBP @5 | 450 |
| TBP @10 | 599 |
| TBP @15 | 734 |
| TBP @20 | 831 |
| TBP @30 | 953 |
| TBP @40 | 1033 |
| TBP @50 | 1096 |
| TBP @60 | 1157 |
| TBP @70 | 1220 |
| TBP @80 | 1284 |
| TBP @90 | 1332 |
| TBP @95 | 1357 |
| TBP @99.5 | 1384 |
| Physical Properties: | |
| VI | 140 |
| VIS@100° C. | 7.34 CST |
| VIS@40° C. | 42 CST |
| Pour Point | −54° C. |
| Cloud Point | <−52° C. |
| Bromine # | 3.1 |

As shown in the data above, high quality oils with desirable lubricating properties can be made by either simultaneous olefin oligomerization/alkylation, or by oligomerization of the appropriate olefins followed by alkylation of the oligomeric products. Regardless of the process, the oils produced in both processes appear to be close in their boiling ranges, olefinicity and physical properties such as viscosity indices, viscosities, pour points and cloud points. Both process lead to oils with appreciable concentrations of branched paraffins formed by capping (alkylating) olefins and their oligomers and low olefin concentrations.

Example 7

FCC Naphtha

A sample of a naphtha produced at Chevron's Pascagoula FCC unit was analyzed and determined to have the hydrocarbon types summarized below:

TABLE 7

| Hydrocarbon Types | Wt % |
|---|---|
| N-Paraffins | 4.560 |
| Iso-Paraffins | 23.674 |
| Naphthenes | 7.900 |
| Olefins | 29.111 |
| Aromatics | 34.755 |
| Total | 100.000 |

This sample of FCC naphtha had a range of C5 to C15 olefins. The olefins were both alpha olefins and internal olefins. There were a higher amount of internal olefins than alpha olefins. Additionally, the FCC naphtha had a range of C5 to C14 isoparaffins.

A separate sample of FCC gas from a recent pilot plant FCC unit run had a mix of C2 to C7 olefins and C3 to C7 isoparaffins.

The broad range of olefins with different carbon numbers and olefin placement make the olefins from a FCC unit useful in the processes described herein.

What is claimed is:

1. A process to make two or more viscosity grades of base oil, comprising:
   a. alkylating and oligomerizing an olefin feed produced by thermal cracking of a waxy feed with an acidic ionic liquid catalyst comprising a chloroaluminate in a common oligomerization-alkylation zone to produce an alkylated oligomeric product; and
   b. separating out two or more viscosity grades of base oil from the alkylated oligomeric product, wherein at least one of the two or more viscosity grades of base oil has:
      i. a kinematic viscosity at 100° C. of 6.9 mm2/s or greater,
      ii. a VI of at least 134,
      iii. a Bromine Number of less than 4, and
      iv. a cloud point less than −30° C.

2. The process of claim 1, wherein a set of alkylation conditions in the alkylation zone are selected to optimize a yield of one of the two or more viscosity grades of base oil.

3. The process of claim 1, wherein the olefin feed is from a FCC unit, a coker, or a wax cracker.

4. The process of claim 1, wherein the acidic ionic liquid catalyst comprises a 1-butyl-pyridinium chloroaluminate.

* * * * *